United States Patent [19]

Hutson, Jr.

[11] 4,373,110

[45] Feb. 8, 1983

[54] HF ALKYLATION PROCESS AND APPARATUS

[75] Inventor: Thomas Hutson, Jr., Bartlesville, Okla.

[73] Assignee: Phillips Petroleum Company, Bartlesville, Okla.

[21] Appl. No.: 226,589

[22] Filed: Jan. 21, 1981

[51] Int. Cl.³ .......................... C07C 2/56; C07C 2/58; C07C 2/62
[52] U.S. Cl. .................................... 585/719; 585/723; 422/234; 422/235
[58] Field of Search ................ 585/719, 723; 422/234, 422/235

[56] References Cited

U.S. PATENT DOCUMENTS

| | | | |
|---|---|---|---|
| 2,984,693 | 5/1961 | Cabbage | 260/683.42 |
| 3,069,483 | 12/1962 | Bauer | 260/683.48 |
| 3,213,157 | 10/1965 | Hays et al. | 260/683.48 |
| 3,431,079 | 3/1969 | Chapman | 422/235 |
| 3,721,720 | 3/1973 | Chapman et al. | 260/683.48 |
| 3,767,726 | 10/1973 | Hutson et al. | 585/719 |
| 3,804,918 | 4/1974 | Henderson | 422/235 |
| 3,867,473 | 2/1975 | Anderson | 260/683.45 |
| 3,919,342 | 11/1975 | Chapman | 260/683.42 |
| 3,919,343 | 11/1975 | Sobel et al. | 260/683.48 |
| 3,993,706 | 11/1976 | Mikulicz et al. | 260/683.48 |
| 4,041,101 | 8/1977 | Sobel | 260/683.51 |
| 4,195,191 | 3/1980 | Boney | 585/706 |
| 4,236,036 | 11/1980 | Dixon et al. | 585/719 |
| 4,249,030 | 2/1981 | Chapman et al. | 422/235 |

FOREIGN PATENT DOCUMENTS

294171  2/1967  Australia ............................ 585/719

*Primary Examiner*—Delbert E. Gantz
*Assistant Examiner*—Helane E. Maull

[57] ABSTRACT

Acid soluble oils recovered from the acid phase from an HF alkylation unit are processed with hydrocarbon phase from the same or a different unit.

30 Claims, 2 Drawing Figures

HF ALKYLATION PROCESS AND APPARATUS

BACKGROUND OF THE INVENTION

In one aspect the invention relates to hydrocarbon processing. In another aspect, the invention relates to an alkylation process. In yet another aspect, the invention relates to an apparatus for carrying out an alkylation process.

Alkylation processes are often employed by the petrochemical and refining industries to produce high octane blending stocks for gasoline. In such processes, it is inevitable that a portion of the feedstock, commonly at least one isoparaffin and at least one olefin, react in a manner to form a hydrocarbon having a molecular weight higher than that of the desired alkylate product. At least a portion of this hydrocarbon comprises a polymeric material which is more soluble in acid than in hydrocarbon and is commonly referred to by the industry as acid soluble oil, or "ASO". Acid soluble oils build-up in liquid acid alkylation catalyst systems and are desirably periodically or continuously removed so as to be maintained at low levels in liquid acid alkylation catalyst systems.

It is further desirable to at least partially remove water and light hydrocarbons such as propane from alkylation systems to prevent their build-up and interference with process performance. Such materials are sometimes intentionally or unintentionally introduced into alkylation systems.

According to U.S. Pat. No. 3,721,720, issued Mar. 20, 1973 to C. C. Chapman et al, the disclosure of which is incorporated herein by reference, acid soluble oils and water can be removed from hydrogen fluoride (HF) catalyst by processing a slip stream of catalyst in a fractionator under controlled temperature and pressure conditions. The acid soluble oil stream, which is removed as fractionator bottoms, is a small stream and contains only small amounts of HF and water, ASO being the major component. The ASO stream is recycled to the refinery or passed to a disposal unit.

According to U.S. Pat. No. 3,069,483, issued Dec. 18, 1962 to R. D. Bauer, the disclosure of which is hereby incorporated by reference, excessive propane build-up in an HF alkylation system can be prevented by processing a slip stream of the hydrocarbon phase in a depropanizer.

According to U.S. Pat. No. 2,984,693, issued May 16, 1961 to J. T. Cabbage, the disclosure of which is hereby incorporated by reference, excessive propane build-up in an HF alkylation system can be prevented by charging the hydrocarbon phase to an isobutane column and the overhead from the isobutane column to a depropanizer. Controlled reboiler conditions thermally decompose organically combined fluorine predominately in the $C_3$-$C_4$ range.

In U.S. Pat. No. 3,993,706, issued Nov. 23, 1976 to Mikulicz et al, the hydrocarbon phase is charged to an isobutane column and the overhead from the isobutane column is charged to a depropanizer to prevent excessive propane build-up in the alkylation system. A portion of the HF catalyst phase, the major portion of which is HF, is dissolved in the overhead from the isobutane column and enters the depropanizer. In the depropanizer, the HF is separated from the ASO and recycled. The ASO is recovered as bottoms from the depropanizer and passes to the isobutane column from which it is recovered as bottoms in a blend with alkylate product.

OBJECTS OF THE INVENTION

It is an object of this invention to provide an alkylation system which provides for recovery of acid soluble oils as a useful product.

It is a further object of this invention to provide a system for the recovery of acid soluble oils which is readily adapted for installment on existing alkylation units.

It is a still further object of this invention to provide a system for the recovery of acid soluble oils in which only a small amount of dilute HF is present in the acid soluble oil to pass into the product separation equipment.

It is yet another object of this invention to provide apparatus suitable for implementing the improved system.

STATEMENT OF THE INVENTION

According to one embodiment of the present invention, polymer material (ASO) is separated from a portion of the HF acid phase in an alkylation unit. At least a portion of this polymer material is combined with at least a portion of the hydrocarbon phase from the unit. From these combined materials, there is separated an alkylate product which contains polymer material. According to this embodiment, separation of the polymer material from a portion of the HF acid phase and routing the polymer material to product separation can reduce the amount of HF acid entering the product separation zone from that of U.S. Pat. No. 3,993,706. When the amount of HF is small, corrosion problems within the product separation zone are reduced, and the use of expensive materials of construction, such as monel, can be avoided.

According to another embodiment of the invention, a process in which isoparaffin feedstock is reacted with olefin feedstock in the presence of hydrogen fluoride catalyst to form a reaction effluent which is separated into a hydrocarbon phase and an HF acid phase, wherein the hydrocarbon phase is passed to a separation zone for the separation and recovery of alkylate product and a portion of the HF acid phase is passed to a separation zone for the separation of polymeric material from the major portion of the HF, is improved by passing at least a portion of the polymeric material to the separation zone for the separation of alkylate product. In this embodiment, polymeric materials are recovered in blend with alkylate product, as contrasted to prior art processes in which the acid soluble oils were disposed of in a neutralizing pond or recycled to other refinery processes, such as by being blended with catalytic cracking feed. When the separation zone is provided with high temperature reboiling means, the acid soluble oils can be upgraded by at least partial defluorination.

In a still further embodiment of the present invention, an HF alkylation unit comprising an HF alkylation reactor with settler, and an HF acid catalyst regenerator and an alkylate product separator each in flow communication with the settler is improved by provision of a conduit means for withdrawing polymeric material from the HF acid regenerator and conveying the polymeric material to the alkylate product separator.

DETAILED DESCRIPTION OF THE INVENTION

As used herein, the term "isoparaffin" relates to isoparaffin feedstock or recycle to an HF alkylation reactor, to avoid confusion with the product alkylate, which is also technically an isoparaffin.

The term "polymeric material" is intended to include "acid soluble oils" as well as possible products resulting from the contact of acid soluble oils with elevated temperatures below that at which cracking commences.

Figure 1:
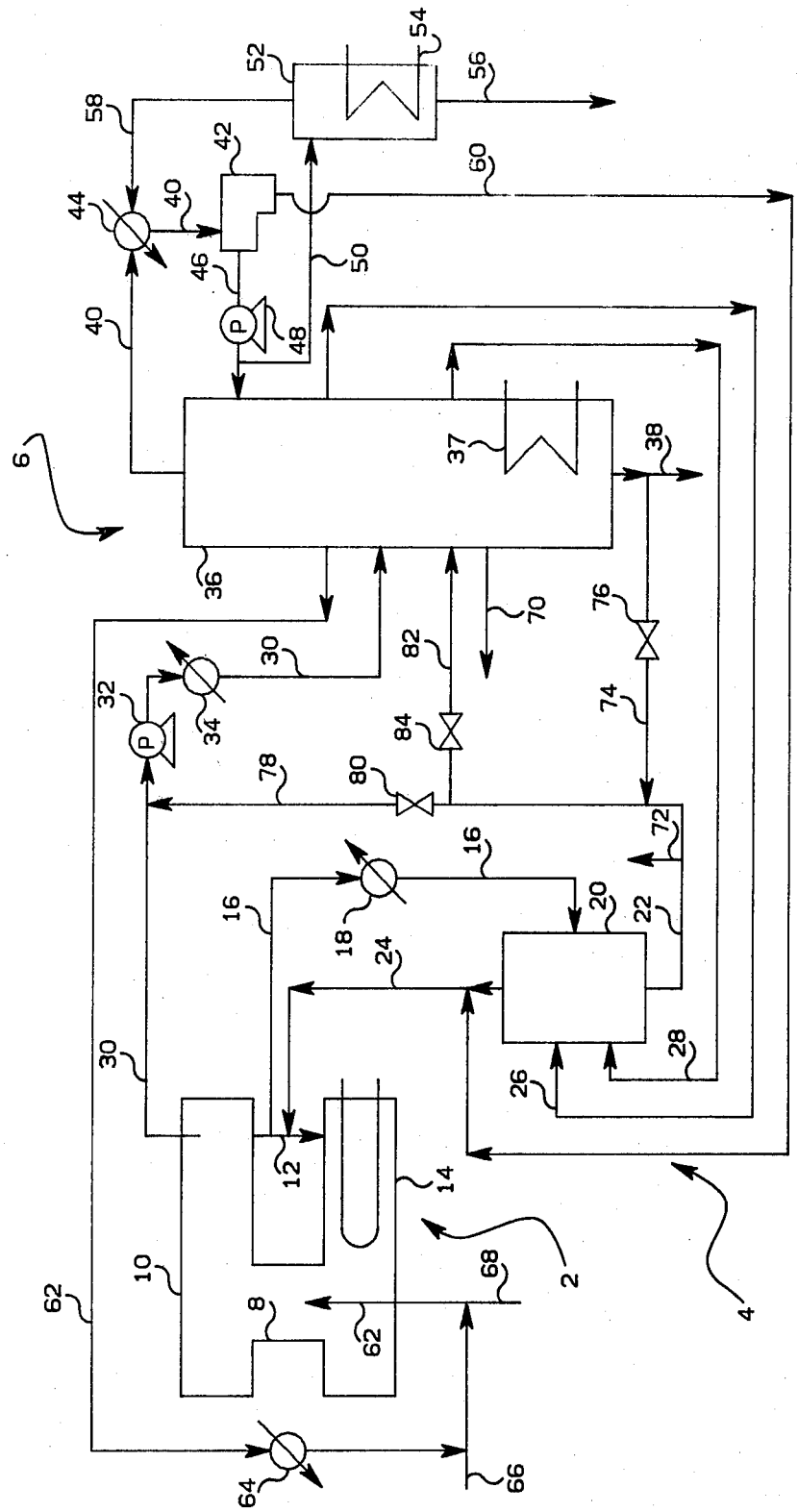
FIG. 1 illustrates in schematic certain features of one embodiment of the present invention.

With reference to FIG. 1, an alkylation unit comprises a means 2 for conducting an alkylation reaction, a means 4 for regenerating alkylation catalyst, and a means 6 for recovery of alkylate product.

The means 2 preferably comprises a means 8 for contacting an alkylation catalyst, such as hydrogen fluoride, with an isoparaffin, such as isobutane or isopentane, preferably isobutane, and at least one olefin, preferably an olefin selected from the group consisting of propene, butene-1, butene-2, isobutene, and pentenes. Preferably, the means 8 is a riser-reactor.

The means 8 opens into a means 10 for phase separating a liquid hydrocarbon phase from a liquid catalyst phase. Preferably, the means 10 comprises a settler vessel of sufficient size to provide for the establishment of an upper hydrocarbon phase and a lower HF phase therein.

A conduit means 12 leads from a lower portion of the settler vessel 10 to a means 14 for cooling catalyst. Preferably, the means 14 comprises a shell and tube heat exchanger. Cooling fluid, such as relatively cool cooling water, is circulated through the tube side of the heat exchanger bundle for indirect heat exchange with the acid on the shell side. The shell side of the heat exchanger 14 communicates with the riser reactor 8 to provide for loop flow of catalyst through the riser-reactor 8, the settler 10, the line 12, and the heat exchanger 14.

A conduit means 16 for withdrawing a slip stream of system catalyst from the reactor 2 establishes communication between a lower portion of the settler vessel 10 and the means 4 for regenerating catalyst. As shown, the conduit 16 extends from the conduit 12, although other arrangements can be employed if desired. Preferably, the means 16 includes a heat exchanger 18 for indirectly heating and vaporizing the major portion of the contents of the conduit 16 before same are introduced into the means 4, which is the zone in which polymeric material and water if present in excessive quantities is separated from the catalyst.

The means 4 preferably comprises a fractionator or rerun column 20. The fractionator 20 is employed to separate polymeric material from the alkylation catalyst. Preferably, a stream of polymeric material is separated from the alkylation catalyst which contains polymeric material as its major component. Usually, the stream contains water and HF as well, but preferably in a combined amount of only about 5% by volume or less. It is desirable to maintain the fractionator 20 under appropriate conditions so that water which may be present in the catalyst inventory in an amount in excess of about 1% by weight is separated from the catalyst with the polymeric material in the fractionator. Most preferably, the reactor feedstocks are suitably treated to prevent water accumulation in the catalyst system. Water and polymeric material are withdrawn from the fractionator 20 by a conduit means 22 communicating with a lower portion of the fractionator 20 for withdrawing water and polymeric material from the acid regenerator 4. A conduit 24 communicating with an upper portion of the fractionator 20 conveys regenerated catalyst vapor and isobutane vapor back to the alkylation reactor 2, preferably into the hydrocarbon phase of settler 10. Reflux liquid, preferably isobutane, is introduced adjacent the upper portion of the fractionator 20 via a conduit 26. Stripping vapor, preferably isobutane, is introduced adjacent the lower portion of the fractionator 20 via a conduit 28.

A conduit means 30 establishes communication between an upper portion of the settler 10 and the means 6 for recovering alkylate product. Preferably, the means 30 includes a pump 32 and a heat exchanger 34. At least a portion of the hydrocarbon phase in the settler 10 is withdrawn by the conduit 30 due to the action of pump 32, heated in heat exchanger 34, and passed to the means 6 which is the zone in which separation of alkylate product occurs.

Preferably, the means 6 comprises at least one fractionator. As shown in FIG. 1, the conduit 30 empties into a fractionator 36 which is provided with a reboiler means 37. Alkylate product is withdrawn from a lower portion of the fractionator 36 via a conduit 38. Hydrogen fluoride and light hydrocarbon, such as propane, are withdrawn from an upper portion of the fractionator 36 by a conduit 40 which empties into an accumulator 42. A condenser 44 is associated with the conduit 40. The light hydrocarbon and hydrogen fluoride issuing from the fractionator 36 are condensed in the condenser 44 and pass to the accumulator 42, where the mass separates into an upper light hydrocarbon liquid phase and a lower HF liquid phase. A conduit means 46 for withdrawing light hydrocarbon from the accumulator 42 communicates with an upper portion of the accumulator 42. A pump 48 is associated with the conduit 46. The conduit 46 empties into the fractionator 36 adjacent its upper portion to provide light hydrocarbon reflux. A means 50 for withdrawing a stream of the light hydrocarbon liquid phase from the accumulator 42 opens preferably from the conduit 46 between the pump 48 and the fractionator 36 to take advantage of the pump 48. The means 50 empties into a fractionator or stripper 52 provided with a reboiling means 54. Liquid light hydrocarbon product is withdrawn from a lower portion of the fractionator 54 via a conduit 56. Overhead vapor from the fractionator 52 is withdrawn by a conduit 58, condensed, and passed back to the accumulator 42. Preferably, the conduit 58 empties into the conduit 40 upstream of the condenser 44 to avoid duplication of condensers. A conduit means 60 establishes communication between a lower portion of the accumulator 42 and the alkylation reactor 2 for recycle of liquid HF catalyst liquid.

Unreacted liquid isoparaffin for recycle is withdrawn from the fractionator 36 by a conduit 62 communicating adjacent the upper portion of the fractionator 36. The isoparaffin carried by the conduit 62 is cooled in a heat exchanger 64, combined with feed isoparaffin introduced via the conduit 66, and feed olefin introduced via the conduit 68 and introduced into the riser reactor 8.

A side cut from the fractionator 36, comprising vaporous n-butane, can be withdrawn by a conduit 70 communicating with an intermediate portion of the fractionator 36. The fractionator 36 also provides a convenient source for reflux liquid and stripping vapor for the acid regenerator 4. As shown, the conduits 26 and 28 each establish communication between the fractionator 36 and the fractionator 20.

According to one embodiment of the invention, the conduit means 22 for withdrawing polymeric material from the fractionator 20 is routed so as to convey at least a portion of the polymeric material to the means 6 for separating alkylate product. Preferably, the conduit means 22 is constructed of monel or other suitable material resistant to HF attack. If desired, for example, in the event of excessive water in the conduit 22, a portion of the contents of the conduit 22 can be drawn off for proper and safe disposal via a conduit 72 communicating with the conduit 22. It is preferable to dilute the contents of the conduit 22 with a suitable diluent prior to conveying the polymeric material and water to the means 6, to aid handling. To this end, a conduit means 74 having a valve 76 therein establishes communication between the conduit 38 and the conduit 22. A portion of the contents of the conduit 38 can thus be blended with at least a portion of the contents of the conduit 22. Preferably, the conduit 74 opens into the conduit 22 closely adjacent the fractionator 20. Product alkylate containing polymeric material withdrawn from the acid regenerator is yielded at 38.

In the embodiments illustrated in FIG. 1, the contents of the conduit 22 can discharge into the conduit 30 via conduit 78 having valve 80 disposed therein establishing communication between the conduit 22 and the conduit 30 and/or be discharged directly into the fractionator 36 via conduit 82 having valve 84 disposed therein which establishes communication between conduit 22 and fractionator 36.

Figure 2:
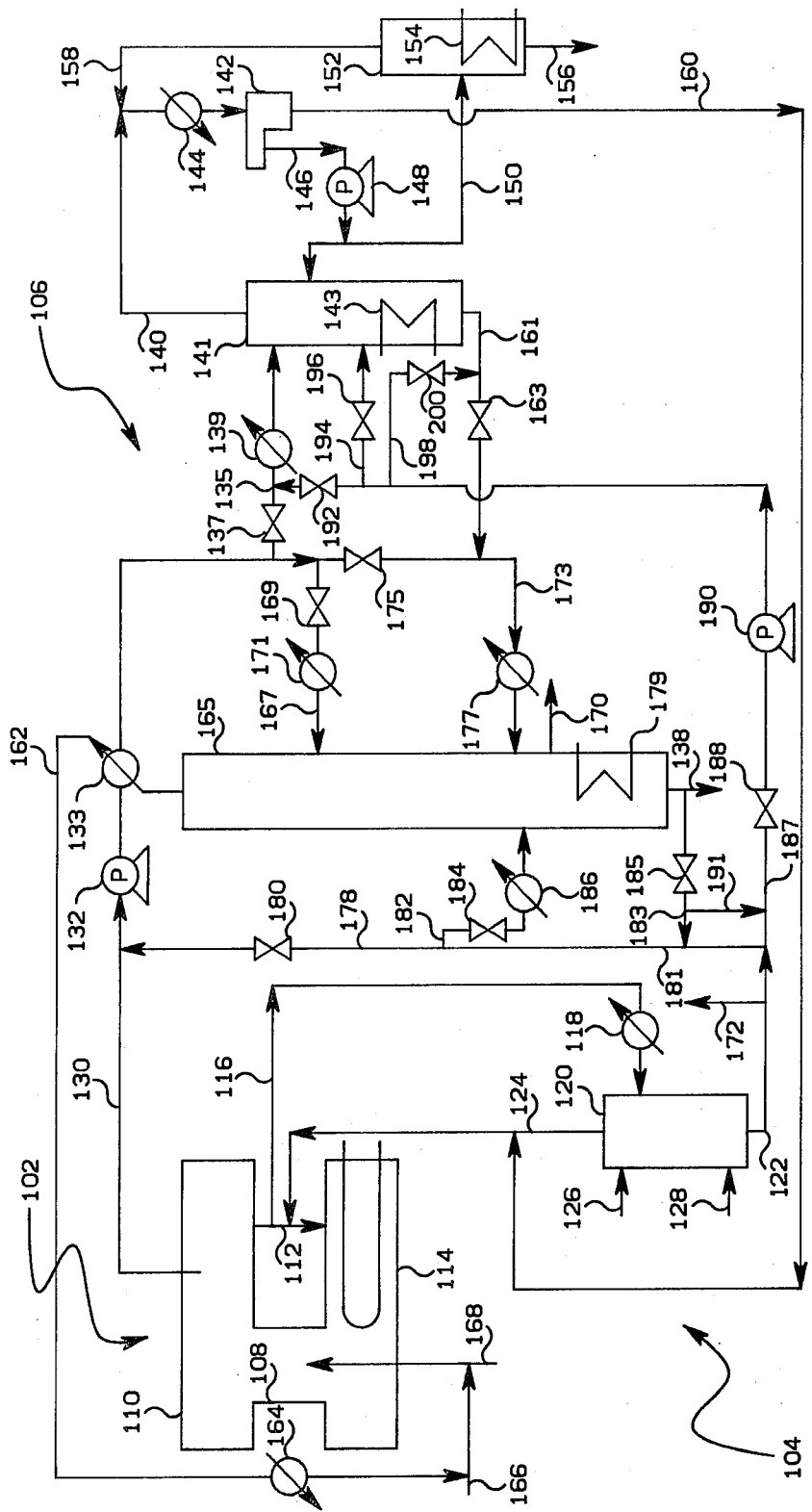
FIG. 2 illustrates in schematic certain features of another embodiment of the present invention.

The embodiment of the invention illustrated in FIG. 2 comprises a means 102 for carrying out an alkylation reaction, a means 104 for regenerating alkylation catalyst, and a means 106 for recovering alkylate product.

The means 102 preferably comprises a means 108 for contacting an alkylation catalyst, such as liquid hydrogen fluoride, with a liquid isoparaffin, preferably isobutane, and at least one liquid olefin, preferably an olefin selected from the group consisting of propene, butene-1, butene-2, isobutene, and pentenes. Preferably, the means 108 is a riser-reactor.

The means 108 opens into a means 110 for phase separating a liquid hydrocarbon phase from a liquid catalyst phase. Preferably, the means 110 comprises a settler vessel of sufficient size to provide for the establishment of an upper liquid hydrocarbon phase and a lower liquid HF phase therein.

A conduit means 112 leads from a lower portion of the settler vessel 110 to a means 114 for cooling catalyst. Preferably, the means 114 comprises a shell and tube heat exchanger. Cooling fluid, such as relatively cool cooling water, is circulated through the tube side of the heat exchanger bundle for indirect heat exchange with the liquid HF acid on the shell side. The shell side of the heat exchanger 114 communicates with the riser-reactor 108 to provide for loop flow of catalyst through the riser-reactor 108, the settler 110, the line 112, and the heat exchanger 114.

A means 116 for withdrawing a slip stream of catalyst from the reactor 102 establishes communication between a lower portion of the settler vessel 110 and the means 104 for regenerating catalyst. As shown, the conduit 116 extends from the conduit 112, although other arrangements can be employed if desired. Preferably, the means 116 includes a heat exchanger 118 for indirectly heating the contents of the conduit 116 before same are introduced into the means 104, which is the zone in which polymeric material and water are separated from the catalyst.

The means 104 preferably comprises a fractionator or rerun column 120. The fractionator 120 is employed to separate water, when present in higher than desired quantities, and polymeric material from the alkylation catalyst. Water and polymeric material are withdrawn from the fractionator 120 by a conduit means 122 communicating with a lower portion of the fractionator 120 for withdrawing water and polymeric material from the acid regenerator 104. Preferably the polymeric material is the main component of the stream carried by the conduit 122. A conduit 124 communicating with an upper portion of the fractionator 120 conveys regenerated catalyst vapor and isobutene vapor back to the alkylation reactor 102. Reflux liquid, preferably isobutane, is introduced adjacent the upper portion of the fractionator 120 via a conduit 126. Stripping vapor, preferably isobutane, is introduced adjacent the lower portion of the fractionator 120 via a conduit 128.

A conduit means 130 establishes communication between an upper portion of the settler 110 and the means 106 for recovering alkylate product. Preferably, the means 130 includes a pump 132 and a heat exchanger 133. At least a portion of the hydrocarbon phase in the settler 110 is withdrawn by the conduit 130 due to the action of pump 132, heated in heat exchanger 133, and passed to the means 106 which is the zone in which separation of alkylate product occurs.

The means 106 comprises a fractionator 141 and a fractionator 165. Preferably, the fractionator 141 is a depropanizer and the fractionator 165 is an isobutane column. A conduit means 135 for withdrawing at least a stream of the hydrocarbon phase from the conduit 130 establishes communication between the conduit 130 and the fractionator 141. Preferably, the conduit means 135 includes a valve 137 and a heat exchanger 139, to further heat the material in conduit 135.

The fractionator 141 is provided with a reboiler means 143. Hydrogen fluoride and light hydrocarbon, such as propane, are withdrawn from an upper portion of the fractionator 141 by a conduit 140, which empties into an accumulator 142. A condenser 144 is associated with the conduit 140. In the accumulator 142, the hydrogen fluoride and light hydrocarbon separate into an upper liquid hydrocarbon phase and a lower liquid HF phase. A conduit means 146 for withdrawing light hydrocarbon from the accumulator 142 communicates with an upper portion of the accumulator 142 and empties into an upper portion of the fractionator 141. A pump 148 is associated with the conduit 146. Downstream of pump 148 a means 150 for withdrawing a stream from the conduit 146 establishes a flow path between the conduit 148 and a fractionator 152 which is provided with a reboiler means 154. Light liquid hydrocarbon product is withdrawn from the fractionator 152 by a conduit 156 communicating with a lower portion thereof. Overhead vapor from the fractionator 152 is passed back to the accumulator 142 via c conduit 158, which preferably empties into the conduit 140 upstream of the condenser 144. A conduit means 160 establishes communication between a lower portion of the accumulator 142 and the alkylation reactor 2 for recycle of recovered HF catalyst liquid.

Bottoms product from the fractionator 141 is withdrawn by a conduit 161 having a valve 163 disposed therein and charged to the fractionator 165. The contents of the conduit 161 can be either blended with the contents of the conduit 130 and charged to the column, or charged directly to the column 165, as desired. In the embodiment shown, the conduit 130 empties into a conduit 167 having a valve 169 and a heat exchanger 171 (for heating) disposed therein and a conduit 173 having a valve 175 and a heat exchanger 177 (for heating) disposed therein. By closing valve 175, the contents of the conduit 130 and those of the conduit 161 can be charged separately into the fractionator 165 via conduits 167 and 173, respectively. By closing the valve 169 and opening the valve 175, the contents of the conduit 130 and those of the conduit 161 are introduced into the fractionator 165 in admixture via conduit 173. Of course, both valves can be open if desired.

The fractionator 165 is provided with a reboiler 179. Isoparaffin vapor for recycle is withdrawn from an upper portion of the fractionator 165 via a conduit 162. The isoparaffin is cooled in heat exchanger 133 and provides preheat for the contents of the conduit 130. If necessary, the isoparaffin is further cooled in a heat exchanger 164 for complete condensing and cooling before being combined with feed isoparaffin introduced into the conduit 162 via a conduit 166, with feed olefin introduced into the conduit 162 via a conduit 168 and introduced into the riser-reactor 8.

A sidedraw conduit 170 is provided for removal for n-paraffin, such as vaporous n-butane, from the fractionator 165.

Alkylate product is removed from the fractionator 165 via conduit 138 which communicates with a lower portion of the fractionator 165.

At least a portion of the polymeric material carried by the conduit 122 is introduced into the product separation zone 106. If desired, for example, in the event of excessive water in the conduit 122, a portion of the contents of the conduit 122 can be drawn off for proper safe disposal via conduit 172 communicating with the conduit 122. It is preferable that the conduit means 122 be constructed of monel or other suitable material resistant to HF attack. The contents of the conduit 122 can be charged to the fractionator 165 and/or the depropanizer 141. Some of the various possibilities are illustrated by FIG. 2. For example, the conduit 122 can empty into a conduit 181. A conduit 183 having a valve 185 disposed therein establishes communication between the conduit 138 and the conduit 181 for supply of alkylate diluent. The conduit 181 empties into a conduit 178 which has a valve 180 disposed therein and which empties into the conduit 130. The conduit 181 can also empty into a conduit 182 which in turn empties into the fractionator 165. The conduit 182 is preferably provided with a valve 184 and a heat exchanger (heater) 186. If desired, the conduit 122 can empty into a conduit 187 having a valve 188 and a pump 190 associated therewith. A conduit 191 communicating between the conduit 183 and the conduit 187 provides a flow path between the conduit 138 and the conduit 187 for dilution of the polymeric material with alkylate. The contents of the conduit 187 can be discharged into the line 135, if desired, via the valve 192, and/or, if desired, directly into the depropanizer 141 via the line 194 and the valve 196, and/or, if desired, into the depropanizer bottoms line 161 via the line 198 and the valve 200.

With reference to FIG. 1, there is provided in the settler vessel 10 a reaction mixture comprising hydrogen fluoride, isoparaffin and the reaction products of isoparaffin and olefin in the presence of hydrogen fluoride. This is generally accomplished by carrying out in the riser-reactor 8 an alkylation of isoparaffin with olefin with a substantial molar excess of isoparaffin to olefin usually to provide a feed ratio in excess of 1:1, usually from about 4:1 to about 20:1 and preferably from about 10:1 to 15:1 of isoparaffin to olefin. The riser-reactor 8 is maintained under sufficient pressure to ensure that the hydrocarbon reactants and alkylation catalyst are in the liquid phase. The temperature of the reaction will vary with the reactants and with the catalyst employed, but generally ranges from about $-40°$ F. to about 150° F. In the settler vessel 10, the reaction mixture is separated into a first phase containing liquid hydrocarbon as its major component and a second phase containing liquid hydrogen fluoride catalyst as its major component and polymeric material as a minor component. A first stream is withdrawn from the first phase via the line 30 which contains hydrocarbon as its major component. From the portion of the second phase which is withdrawn from the reactor 2 via the line 16, there is separated the stream 22 which contains polymeric material, preferably, as its major component. At least a portion of the stream contained in the conduit 22 is combined with at least a portion of the first stream flowing through the conduit 30, for example by passage of the contents of the conduit 22 through line 78, in which event the streams are combined prior to introduction to fractionator 36, and/or line 82, in which event the streams are combined in the fractionator 36. From the combined at least a portion of the first stream and the at least a portion of the second stream there is separated a third stream carried by the conduit 38 which contains the reaction products of isoparaffin and olefin as its major component. As used herein, the term "major component" connotes a component which is present at a concentration by volume of greater than 50 percent, while the term "minor component" connotes a component which is present at a concentration of less than 50 percent by volume.

If expedient, a portion of the stream containing polymeric material carried by the conduit 22 can be conveyed away via the line 72 for proper and safe disposal. To aid in handling, it is preferable to combine a portion of the alkylate stream carried by the conduit 38 with the portion of the second stream containing polymeric material to be combined with the stream from the hydrocarbon phase. This is accomplished in accordance with the present invention by manipulating valve 76 to allow fluid flow from the conduit 38 and into the conduit 22.

In the invention as illustrated in FIG. 2, at least a portion of the stream containing polymeric material carried by the conduit 122 can be introduced into the separation zone 106 by combination with at least one of the hydrocarbon streams carried by the conduit 130 and/or 135 by passage through the conduits 178 and 187, respectively; and/or be introduced directly into the fractionators 165 or 141 via the conduits 182 and 194, respectively; and/or be combined with the bottoms stream 161 issuing from the fractionator 141, for example. The polymer-containing stream can be diluted with alkylate from the conduit 138 via conduits 183 and/or 191, as desired. Hydrogen fluoride and propane can be factionated from the combined stream portions by introducing the stream carried by the conduit 122 into the conduit 135 via conduit 187 and/or into the fractionator 141 via conduits 187 and 194.

It is contemplated in the present invention that in operations in which there are two or more alkylation units operating in parallel, the polymeric material recovered from one unit can be passed to the separation zone of the other unit, and, if desired, vice versa. Thus, in this embodiment, at least a portion of the stream of polymeric material is combined with at least a portion of a hydrocarbon phase originating in the same or a different alkylation reactor. is combined with at least a portion of a hydrocarbon phase originating in the same or a different alkylation reactor.

The invention is illustrated by the following example:

CALCULATED EXAMPLE

With reference to FIG. 1, the polymeric material from acid regenerator 20 is combined with the hydrocarbon phase in line 30 via lines 22 and 78. Valve 80 is open, valve 82 is closed. Unit operating conditions are set forth in the following table.

TABLE I

| Operating Conditions: | | |
|---|---|---|
| (8) Alkylation Reactor: | | |
| Pressure, psia, | 150 | (1020 kPa) |
| Temperature (Inlet), °F., | 90 | (32.2° C.) |
| $HF^{(1)}$/Total Hydrocarbon Volume Ratio, | 4:1 | |
| Isobutane/Olefin Volume Ratio, | 14:1 | |
| (20) HF Rerun Column: | | |
| Pressure, psia, | 150 | (1020 kPa) |
| Feed Temperature, °F., | 300 | (148.9° C.) |
| Temperatures, °F., | | |
| Top, | 289 | (142.8° C.) |
| Bottom, | 300 | (148.9° C.) |
| (36) Main Fractionator | | |
| Pressures, psia, | | |
| Top, | 235 | (1600 kPa) |
| Bottom, | 240 | (1635 kPa) |
| Temperatures, | | |
| Top, | 164 | (73.3° C.) |
| Bottom, | 409 | (209.4° C.) |
| (52) HF Stripper | | |

TABLE I-continued

| Operating Conditions: | | |
|---|---|---|
| Pressure, psia, | 330 | (2247 kPa) |
| Temperatures, °F., | | |
| Top, | 134 | (56.7° C.) |
| Bottom, | 148 | (64.4° C.) |

[1]HF catalyst can have up to about 3 volume percent water; up to about 2-3 volume percent ASO; and hydrocarbons of about 2 to 3 volume percent.

Material balances are set forth in the following Table.

TABLE II

BALANCES: BARRELS/DAY[5]

| Composition Stream No. | Propane | Isobutane | Normal Butane | Propylene | Butenes[1] | Isopentane Plus[2] | HF | ASO[4] | Total |
|---|---|---|---|---|---|---|---|---|---|
| Feed isobutane, (66) | 111 | 1991 | 111 | — | — | — | — | — | 2213 |
| Feed Olefins (68) | 157 | 1893 | 539 | 48 | 3324 | 54 | — | — | 6015 |
| Recycle iC$_4$ (62) | 1729 | 43325 | 3348 | — | — | 677 | 119 | 0 | 49198 |
| Total Feed (—) | 1997 | 47209 | 3998 | 48 | 3324 | 731 | 119 | 0 | 57426 |
| Reactor Product, (30) | 2027 | 43893 | 4036 | — | — | 6737 | 376 | 0 | 57079 |
| Rerun Bottoms, (22) | — | 0.05 | — | — | — | — | 0.05 | 5.90 | 6.00 |
| Diluent Alkylate, (74) | — | Trace | 0.25 | — | — | 6.00 | — | Trace | 6.25 |
| Total to 30, (78) | — | 0.05 | 0.25 | — | — | 6.00 | 0.05 | 5.90 | 12.25 |
| Total to Tower 36, | 2027 | 43903.05 | 4036.25 | — | — | 6743 | 376.05 | 5.90 | 57091.25 |
| Propane (56) | 273 | 4 | — | — | — | — | — | — | 277 |
| HF (60) | 6 | 12 | — | — | — | — | 257 | — | 275 |
| Normal Butane (70) | — | 26 | 396 | — | — | 53 | — | — | 475 |
| Vapor iC$_4$ (28) | 13 | 316 | 25 | — | — | 5 | 1 | — | 360 |
| Liquid iC$_4$ (26) | 1 | 32 | 3 | — | — | 0.5 | — | — | 36.5 |
| Alkylate Yield (38) | — | 6 | 254 | — | — | 6001[3] | — | 5.90 | 6266.9 |

[1]Mixed butene-1; butenes-2; isobutene.
[2]Alkylate.
[3]RON Clear of about 95.
[4]Polymeric oil is referred to as ASO, Acid Soluble Oils.
[5]42 U.S. gallons per barrel; 0.1587 meters$^3$/barrel.

While various preferred embodiments have been shown and described in terms of the presently preferred embodiment, reasonable variations and modifications are possible by those skilled in the art, within the scope of the described invention and the appended claims.

That which is claimed is:

1. A process comprising:
   (a) providing a reaction mixture comprising hydrogen fluoride, isoparaffin, and the reaction products of isoparaffin and olefin in the presence of hydrogen fluoride;
   (b) separating the reaction mixture into a first phase containing hydrocarbon as its major component and a second phase containing hydrogen fluoride as its major component and polymeric material as a minor component;
   (c) withdrawing from the first phase a first stream containing hydrocarbon as its major component;
   (d) withdrawing from the second phase a second stream containing hydrogen fluoride as its major component and polymeric material as a minor component;
   (e) fractionating directly at least a portion of the second stream to form a third stream containing polymeric material as its major component;
   (f) combining at least a portion of the third stream with at least a portion of the first stream, wherein the first stream is withdrawn from a first phase which was separated from the same or a different reaction mixture as the second phase; and
   (g) separating from the combined at least a portion of the first stream and the at least a portion of the third stream a fourth stream containing the reaction products of isoparaffin and olefin as its major component.

2. A process as in claim 1 further comprising combining a portion of the fourth stream with the at least a portion of the third stream to be combined with the at least a portion of the first stream.

3. A process as in claim 2 wherein the isoparaffin comprises isobutane and the olefin comprises at least one of propene, isobutene, butene-1, butene-2, and pentenes.

4. A process as in claim 3 wherein the fourth stream is fractionally separated as fractionator bottoms from the combined at least portions of the first stream and third stream.

5. A process as in claim 4 wherein the at least a portion of the first stream and the at least a portion of the third stream are combined prior to the fractional separation of the fourth stream.

6. A process as in claim 4 wherein the at least a portion of the first stream and the at least a portion of the third stream are combined in the fractional separation of the fourth stream.

7. A process as in claim 4 further comprising fractionally separating hydrogen fluoride and propane from at least a portion of the combined at least a portion of the first stream and the at least a portion of the third stream.

8. A process as in claim 7 wherein the at least a portion of the first stream and the at least a portion of the third stream are combined prior to the fractional separation of hydrogen fluoride and propane.

9. A process as in claim 7 wherein the at least a portion of the first stream and the at least a portion of the third stream are combined in the fractional separation of hydrogen fluoride and propane.

10. In a process comprising:
  (a) reacting an isoparaffin with an olefin in the presence of hydrogen fluoride to produce an effluent stream comprising an alkylate product issuing from a reaction zone;
  (b) separating the effluent stream into a hydrocarbon phase comprising hydrocarbon as its major component and an acid phase comprising hydrogen fluoride as its major component and a polymeric material,
  (c) passing the hydrocarbon phase to a first separation zone;
  (d) withdrawing from the first separation zone a first stream comprising light hydrocarbon and hydrogen fluoride; a second stream comprising isoparaffin as its major component, and a third stream comprising alkylate product as its major component;
  (e) passing at least a portion of the first stream to a second separation zone for separating at least a portion of the light hydrocarbon from at least a portion of the hydrogen fluoride in the first stream;
  (f) passing a portion of the acid phase to a third separation zone; and
  (g) withdrawing from the third separation zone a fourth stream comprising hydrogen fluoride and a fifth stream comprising the polymeric material; the improvement comprising
  (h) passing at least a portion of the fifth stream to the first separation zone.

11. In a process comprising:
reacting an isoparaffin with an olefin in the presence of hydrogen fluoride to produce an effluent stream comprising an alkylate product issuing from a reaction zone;
separating the effluent stream into a hydrocarbon phase comprising hydrocarbon as its major component and an acid phase comprising hydrogen fluoride as its major component and a polymeric material;
passing the hydrocarbon phase to a first separation zone;
withdrawing from the first separation zone a first stream comprising light hydrocarbon and hydrogen flouride; a second stream comprising isoparaffin as its major component, and a third stream comprising alkylate product as its major component;
passing a portion of the acid phase to a second separation zone; and
withdrawing from the second separation zone a fourth stream comprising hydrogen fluoride and a fifth stream comprising the polymeric material; the improvement comprising
passing at least a portion of the fifth stream to the first separation zone; and
combining a portion of the third stream comprising alkylate product as its major component with at least a portion of the fifth stream to be passed to the first separation zone.

12. In a process comprising:
reacting an isoparaffin with an olefin in the presence of hydrogen fluoride to produce an effluent stream comprising an alkylate product issuing from a reaction zone;
separating the effluent stream into a hydrocarbon phase comprising hydrocarbon as its major component and an acid phase comprising hydrogen fluoride as its major component and a polymeric material;
passing the hydrocarbon phase to a first fractionator;
withdrawing from the first fractionator a first stream comprising light hydrocarbon and hydrogen fluoride; a second stream comprising isoparaffin as its major component, and a third stream comprising alkylate product as its major component;
passing a portion of the acid phase to a second fractionator; and
withdrawing from the second fractionator a fourth stream comprising hydrogen fluoride and a fifth stream comprising the polymeric material; the improvement comprising
passing at least a portion of the fifth stream to the first fractionator; and
combining a portion of the third stream with the at least a portion of the fifth stream passing to the first fractionator.

13. In a process comprising:
reacting an isoparaffin with an olefin in the presence of hydrogen fluoride to produce an effluent stream comprising an alkylate product issuing from a reaction zone;
separating the effluent stream into a hydrocarbon phase comprising hydrocarbon as its major component and an acid phase comprising hydrogen fluoride as its major component and a polymeric material;
passing the hydrocarbon phase to a first fractionator;
withdrawing from the first fractionator a first stream comprising light hydrocarbon and hydrogen fluoride; a second stream comprising isoparaffin as its major component, and a third stream comprising alkylate product as its major component;

passing a portion of the acid phase to a second fractionator and withdrawing from the second fractionator a fourth stream comprising hydrogen fluoride and a fifth stream comprising the polymeric material; the improvement comprising combining a portion of the third stream comprising alkylate as its major component with at least a portion of the fifth stream; and introducing the stream formed from combining at least a portion of the fifth stream with the portion of the third stream directly into the first fractionator.

14. In a process comprising reacting an isoparaffin with an olefin in the presence of hydrogen fluoride to produce an effluent stream comprising an alkylate product issuing from a reaction zone;

separating the effluent stream into a hydrocarbon phase comprising hydrocarbon as its major component and an acid phase comprising hydrogen fluoride as its major component and a polymeric material;

passing a first portion of the hydrocarbon phase through a first fractionator and into a second fractionator;

withdrawing from the first fractionator a first stream comprising light hydrocarbon and hydrogen fluoride;

passing a second portion of the hydrocarbon phase directly into the second fractionator;

withdrawing from the second fractionator a second stream comprising isoparaffin as its major component;

withdrawing from the second fractionator a third stream comprising alkylate as its major component;

passing a portion of the acid phase into a third fractionator;

withdrawing from the third fractionator a fourth stream comprising hydrogen fluoride; and withdrawing from the third fractionator a fifth stream comprising the polymeric material;

the improvement comprising combining at least a portion of the fifth stream with at least one of the first portion of the hydrocarbon phase and the second portion of the hydrocarbon phase.

15. In a process comprising reacting an isoparaffin with an olefin in the presence of hydrogen fluoride to produce an effluent stream comprising an alkylate product issuing from a reaction zone;

separating the effluent stream into a hydrocarbon phase comprising hydrocarbon as its major component and an acid phase comprising hydrogen fluoride as its major component and a polymeric material;

passing a first portion of the hydrocarbon phase through a first fractionator and into a second fractionator;

withdrawing from the first fractionator a first stream comprising light hydrocarbon and hydrogen fluoride;

passing a second portion of the hydrocarbon phase directly into the second fractionator;

withdrawing from the second fractionator; a second stream comprising isoparaffin as its major component;

withdrawing from the second fractionator a third stream comprising alkylate as its major component;

passing a portion of the acid phase into a third fractionator;

withdrawing from the third fractionator a fourth stream comprising hydrogen fluoride; and withdrawing from the third fractionator a fifth stream comprising the polymeric material;

the improvement comprising combining at least a portion of the fifth stream with a portion of the third stream and passing the thus combined streams into at least one of the first portion of the hydrocarbon phase and the second portion of the hydrocarbon phase.

16. In a process comprising reacting an isoparaffin with an olefin in the presence of hydrogen fluoride to produce an effluent stream comprising an alkylate product issuing from a reaction zone;

separating the effluent stream into a hydrocarbon phase comprising hydrocarbon as its major component and an acid phase comprising hydrogen fluoride as its major component and a polymeric material;

passing a first portion of the hydrocarbon phase through a first fractionator and into a second fractionator;

withdrawing from the first fractionator a first stream comprising light hydrocarbon and hydrogen fluoride;

passing a second portion of the hydrocarbon phase directly into the second fractionator;

withdrawing from the second fractionator a second stream comprising isoparaffin as its major component;

withdrawing from the second fractionator a third stream comprising alkylate as its major component;

passing a portion of the acid phase into a third fractionator;

withdrawing from the third fractionator a fourth stream comprising hydrogen fluoride; and withdrawing from the third fractionator a fifth stream comprising the polymeric material;

the improvement comprising introducing into the first fractionator a stream formed from combining at least a portion of the fifth stream with a portion of the third stream.

17. In a process comprising reacting an isoparaffin with an olefin in the presence of hydrogen fluoride to produce an effluent stream comprising an alkylate product issuing from a reaction zone;

separating the effluent stream into a hydrocarbon phase comprising hydrocarbon as its major component and an acid phase comprising hydrogen fluoride as its major component and a polymeric material;

passing a first portion of the hydrocarbon phase through a first fractionator and into a second fractionator;

withdrawing from the first fractionator a first stream comprising light hydrocarbon and hydrogen fluoride;

passing a second portion of the hydrocarbon phase directly into the second fractionator;

withdrawing from the second fractionator a second stream comprising isoparaffin as its major component;

withdrawing from the second fractionator a third stream comprising alkylate as its major component;

passing a portion of the acid phase into a third fractionator;

withdrawing from the third fractionator a fourth stream comprising hydrogen fluoride; and withdrawing from the third fractionator a fifth stream comprising the polymeric material;

the improvement comprising introducing into the second fractionator a stream formed from combining at least a portion of the fifth stream with a portion of the third stream.

18. In an apparatus comprising:

(a) an HF alkylation reactor including a settler vessel of sufficient size to provide for the establishment of an upper hydrocarbon phase and a lower HF phase therein;

(b) an acid regenerator for separating polymeric material and water from the HF phase in the settler vessel;

(c) a conduit means establishing communication between a lower portion of the settler vessel and the acid regenerator;

(d) a means for separating alkylate product from the hydrocarbon phase in the settler vessel;

(e) a conduit means establishing communication between an upper portion of the settler vessel and the means for separating alkylate product;

the improvement comprising:

a conduit means for withdrawing polymeric material and water from the acid regenerator and conveying said polymeric material and water to the means for separating alkylate product.

19. Apparatus as in claim 18 where the improvement further comprises a means for withdrawing alkylate product from the means for separating alkylate product and conveying a portion of said alkylate product to the conduit means for withdrawing polymeric material and water from the acid regenerator.

20. Apparatus as in claim 19 wherein the means for separating alkylate product comprises a fractionator and wherein the means for withdrawing alkylate product comprises a conduit communicating with a lower portion of the fractionator.

21. Apparatus as in claim 20 wherein the conduit means establishing communication between the upper portion of the settler vessel and the means for separating alkylate product empties into the fractionator and wherein the conduit means for withdrawing polymeric material and water from the acid regenerator empties into the conduit means establishing communication between the upper portion of the settler vessel and the means for separating alkylate product.

22. Apparatus as in claim 20 wherein the conduit means establishing communication between the upper portion of the settler vessel and the means for separating alkylate product empties into the fractionator and wherein the conduit means for withdrawing polymeric material and water from the acid regenerator empties directly into the fractionator.

23. Apparatus as in claim 19 wherein the means for separating alkylate product comprises a first fractionator and a second fractionator and a conduit means establishing communication between a lower portion of the first fractionator and the second fractionator and wherein the means for withdrawing alkylate product comprises a conduit communicating with a lower portion of the second fractionator.

24. Apparatus as in claim 23 wherein the conduit means establishing communication between the upper portion of the settler vessel and the means for separating alkylate product comprises a conduit portion emptying into the first fractionator and a conduit portion emptying into the second fractionator.

25. Apparatus as in claim 24 wherein the conduit means for withdrawing polymeric material and water from the acid regenerator empties into the conduit means establishing communication between the upper portion of the settler vessel and the means for separating alkylate product.

26. Apparatus as in claim 25 wherein the conduit means for withdrawing polymeric material and water from the acid regenerator empties into the conduit portion of the conduit means establishing communication between the upper portion of the settler vessel and the means for separating alkylate product which empties into the first fractionator.

27. Apparatus as in claim 25 wherein the conduit for withdrawing polymeric material and water from the acid regenerator empties into the conduit portion of the conduit means establishing communication between the upper portion of the settler vessel and the means for separating alkylate product which empties into the second fractionator.

28. Apparatus as in claim 25 wherein the conduit for withdrawing polymeric material and water from the acid regenerator empties directly into the first fractionator.

29. Apparatus as in claim 25 wherein the conduit for withdrawing polymeric material and water from the acid regenerator empties directly into the second fractionator.

30. Apparatus as in claim 25 wherein the conduit for withdrawing polymeric material and water from the acid regenerator empties into the conduit establishing communication between the first fractionator and the second fractionator.

* * * * *